United States Patent
Bales et al.

(10) Patent No.: US 9,040,675 B2
(45) Date of Patent: *May 26, 2015

(54) FORMULATIONS FOR NUCLEIC ACID STABILIZATION ON SOLID SUBSTRATES

(71) Applicant: General Electric Company, Schenectady, NY (US)

(72) Inventors: Brian Christopher Bales, Niskayuna, NY (US); Erik Leeming Kvam, Albany, NY (US); Jason Louis Davis, Albany, NY (US)

(73) Assignee: General Electric Company, Niskayuna, NY (US)

( * ) Notice: Subject to any disclaimer, the term of this patent is extended or adjusted under 35 U.S.C. 154(b) by 64 days.

This patent is subject to a terminal disclaimer.

(21) Appl. No.: 13/721,948

(22) Filed: Dec. 20, 2012

(65) Prior Publication Data

US 2013/0289257 A1   Oct. 31, 2013

Related U.S. Application Data

(63) Continuation-in-part of application No. 13/460,076, filed on Apr. 30, 2012.

(51) Int. Cl.

| B01J 20/04 | (2006.01) |
|---|---|
| B01J 20/24 | (2006.01) |
| C12N 15/10 | (2006.01) |
| G01N 1/40 | (2006.01) |

(52) U.S. Cl.
CPC ........... B01J 20/045 (2013.01); B01J 20/24 (2013.01); C12N 15/1006 (2013.01); G01N 1/40 (2013.01)
USPC ...................... 536/23.1; 536/25.42

(58) Field of Classification Search
USPC ............................. 536/23.1, 25.42
See application file for complete search history.

(56) References Cited

U.S. PATENT DOCUMENTS

| 4,540,506 | A | 9/1985 | Jacobson et al. |
|---|---|---|---|
| 5,173,422 | A | 12/1992 | Knowles et al. |
| 5,756,126 | A | 5/1998 | Burgoyne |
| 5,807,527 | A | 9/1998 | Burgoyne |
| 5,939,259 | A | 8/1999 | Harvey et al. |
| 5,981,218 | A | 11/1999 | Rio et al. |
| 6,168,922 | B1 | 1/2001 | Harvey et al. |
| 6,294,203 | B1 | 9/2001 | Burgoyne |
| 6,528,641 | B2 | 3/2003 | Lader |
| 6,602,718 | B1 | 8/2003 | Augello et al. |
| 6,776,959 | B1 | 8/2004 | Helftenbein |
| 6,794,140 | B1 | 9/2004 | Goldsborough |
| 6,867,290 | B2 | 3/2005 | Goldsborough |
| 7,163,793 | B2 | 1/2007 | Kudlicki et al. |
| 7,244,568 | B2 | 7/2007 | Goldsborough |
| 7,250,270 | B2 | 7/2007 | Goldrick et al. |
| 7,282,371 | B2 | 10/2007 | Helftenbein |
| 7,589,184 | B2 | 9/2009 | Hogan et al. |
| 8,025,850 | B2 | 9/2011 | Chan |
| 8,088,576 | B2 | 1/2012 | Gumbrecht et al. |
| 8,158,357 | B2 | 4/2012 | Birnboim et al. |
| 2001/0039010 | A1 | 11/2001 | Burgoyne |
| 2002/0146696 | A1 | 10/2002 | Burgoyne |
| 2003/0143566 | A1 | 7/2003 | Helftenbein |
| 2004/0009496 | A1 | 1/2004 | Eiblmaier et al. |
| 2004/0126783 | A1 | 7/2004 | Bortolin et al. |
| 2005/0123965 | A1* | 6/2005 | Yamashita et al. ............. 435/6 |
| 2006/0099567 | A1 | 5/2006 | Muller-Cohn et al. |
| 2006/0147918 | A1 | 7/2006 | Goldsborough |
| 2007/0117173 | A1 | 5/2007 | Levison et al. |
| 2008/0176209 | A1 | 7/2008 | Muller et al. |
| 2008/0262097 | A1 | 10/2008 | Eady et al. |
| 2009/0053704 | A1 | 2/2009 | Novoradovskaya et al. |
| 2009/0162924 | A1 | 6/2009 | Birnboim |
| 2009/0208919 | A1 | 8/2009 | Utermohlen et al. |
| 2009/0246750 | A1 | 10/2009 | Lloyd et al. |
| 2009/0291427 | A1 | 11/2009 | Muller-Cohn et al. |
| 2010/0173392 | A1 | 7/2010 | Davis et al. |
| 2010/0209957 | A1 | 8/2010 | Hogan et al. |
| 2010/0248363 | A1 | 9/2010 | Hogan et al. |
| 2011/0070585 | A1 | 3/2011 | Ollikka et al. |
| 2011/0081363 | A1* | 4/2011 | Whitney et al. ............ 424/184.1 |
| 2012/0052572 | A1 | 3/2012 | Whitney et al. |
| 2012/0059160 | A1 | 3/2012 | Bitner et al. |
| 2012/0152743 | A1 | 6/2012 | Finehout et al. |
| 2012/0237939 | A1 | 9/2012 | Reed et al. |
| 2013/0289257 | A1 | 10/2013 | Bales et al. |

FOREIGN PATENT DOCUMENTS

| EP | 1484111 A1 | 12/2004 |
|---|---|---|
| EP | 1559784 A2 | 8/2005 |
| EP | 2388312 A1 | 11/2011 |
| WO | 00/66606 A1 | 11/2000 |

(Continued)

OTHER PUBLICATIONS

Search Report and Written Opinion from PCT Application No. PCT/US2013/38576 dated Sep. 6, 2013.

Zhang et al., "RNA analysis from newborn screening dried blood specimens", Human Genetics, vol. 89, Issue 3, May 1992, pp. 311-314.

Kumar et al. "Inhibition of mammalian ribonucleases by endogenous adenosine dinucleotides", 2003 Biochemical and Biophysical Research Communications 300 pp. 81-86.

Cline, et al. "New Water-Soluble Phosphines as Reductants of Peptide and Protein Disulfide Bonds: Reactivity and Membrane Permeability" 2004 Biochemistry 43: pp. 15195-15203.

Search Report and Written Opinion from PCT Application No. PCT/US2013/065821 dated Jan. 29, 2014.

Li, et al, "Kinetics of RNA degradation by specific base catalysis of transesterification involving the 2'-hydroxyl group" Journal American Chemistry Society, 1999, 121 (23) pp. 5364-5372.

(Continued)

Primary Examiner — Ganapathy Krishnan
(74) Attorney, Agent, or Firm — Eileen B. Gallagher (57) ABSTRACT

The present disclosure generally relates to dry solid matrices for the extraction, stabilization, and storage of nucleic acids, particularly RNA, in a dry format under ambient conditions for a prolonged period of time. Methods for collecting and recovering the nucleic acids stored in the dry solid matrix are also described.

23 Claims, 10 Drawing Sheets

(56) References Cited

FOREIGN PATENT DOCUMENTS

| WO | 2007008722 A2 | 1/2007 |
|---|---|---|
| WO | 2009029433 A2 | 3/2009 |
| WO | 2010132508 A2 | 11/2010 |
| WO | 2011131720 A1 | 10/2011 |
| WO | 2012075471 A1 | 6/2012 |
| WO | 2012113907 A2 | 8/2012 |
| WO | 2013066249 A1 | 5/2013 |

OTHER PUBLICATIONS

Zale, et al. "Why does ribonuclease irreversibly inactivate at high temperatures?", Biochemistry, 1986, 25 (19) pp. 5432-5444.

Natarajan, et al. "Paper-based archiving of mammalian and plant samples for RNA analysis" BioTechniques, 2000, 29 pp. 1328-1333.

Matsubara, et al., "Dried blood spot on filter paper as a source of mRNA", Nucleic Acids Research, vol. 20, Issue 8, Apr. 25, 1992, p. 1998 1 Page.

Sambrook, J. et al. "Molecular Cloning: a Laboratory Manual, 2nd edition" Cold Spring Harbor, New York, Cold Spring Harbor Laboratory Press, Dec. 1989, vol. 1, pp. 7.2, 7.3, 7.4 and 7.5.

Tan et al., DNA, RNA, and Protein Extraction: The Past and The Present, Journal of Biomedicine and Biotechnology, pp. 1-10, 2009.

Ambion Technotes, "Maximize Your RNA Yield: What Yield to Expect", vol. No. 8, Issue No. 3, pp. 1, 13-14, I, May 18, 2001.

Ambion, "RNAqueousTM-4PCR Instruction Manual passage", RNAqueous-4PCR Instruction Manual, pp. 1-29, Apr. 18, 2002.

PCT Search Report and Written Opinion issued in connection with corresponding Application No. PCT/EP2014/067453 on Dec. 19, 2014.

European Search Report issued in connection with corresponding EP Application No. 13784927.9 on Jan. 29, 2015.

* cited by examiner

FORMULATIONS FOR NUCLEIC ACID STABILIZATION ON SOLID SUBSTRATES

CROSS REFERENCE TO RELATED APPLICATIONS

This application is a continuation-in-part of U.S. patent application Ser. No. 13/460,076, filed on Apr. 30, 2012, which is herein incorporated by reference in its entirety.

FEDERALLY SPONSORED RESEARCH & DEVELOPMENT

This invention was made with Government support under contract number (HR0011-11-00127) awarded by the Defense Advanced Research Projects Agency. The Government has certain rights in the invention.

FIELD OF THE INVENTION

The present disclosure generally relates to dry solid substrates and methods of their use for ambient extraction, stabilization, and preservation of nucleic acids, particularly RNA, from a biological sample in a dry format. Methods for extracting, collecting, preserving, and recovering nucleic acids from the dry solid substrates are also described.

BACKGROUND

RNA is one of the most difficult biomolecules to stabilize as a consequence of both chemical self-hydrolysis and enzyme-mediated degradation. Accordingly, the extraction and preservation of RNA derived from a biological sample is sensitive to a number of environmental factors including but not limited to the buffer used to extract or collect the RNA, pH, temperature, and particularly the ubiquitous presence of robust ribonucleases (RNases). As a result, RNA in both purified and unpurified states has typically required storage at −80° C. to prevent hydrolysis and enzymatic degradation and preserve the integrity of the RNA sample. The capability to extract, collect, and preserve RNA under ambient conditions is economically desirable in order to avoid the costs and space requirements associated with refrigeration or freezing samples at −80° C.

Current methodologies for preserving RNA under ambient conditions in a liquid state have focused on deactivation of RNases through the use of, for example, detergents, chaotropic compounds, reducing agents, transitional metals, organic solvents, chelating agents, proteases, RNase peptide inhibitors, and anti-RNase antibodies. Additional efforts have focused on modifying RNA chemically in order to prevent trans-esterification and self-hydrolysis. Most commercially available RNA preservation products but can only preserve RNA in a liquid state for days or weeks at room temperature. Current technologies that claim successful collection and preservation of RNA in a dry format typically require that the RNA is first "pre-purified" and concentrated from the biological material (e.g., biological samples such as blood, serum, tissue, saliva, etc.) prior to storage of the RNA.

Current technologies for the preservation of RNA in a dry format require additional drying facilities. These methods are therefore not conducive to direct RNA collection from a sample (e.g., a biological sample) without significant sample processing.

Accordingly, compositions and methods that integrate RNA extraction, stabilization, and storage/preservation from a sample (e.g., a biological sample) within a single process are desirable and needed in the art. Such compositions and methods would permit long-term storage of RNA under ambient conditions and allow the intact RNA to be recovered for further analysis.

BRIEF DESCRIPTION

A solid matrix for the extraction and storage of nucleic acids from a sample, such as a biological sample as defined herein below, wherein a composition comprising a protein denaturant, a reducing agent, a buffer, and optionally a free-radical trap or RNase inhibitor is present in the solid matrix in a dried format is described. In one embodiment, the dry solid matrices of the instant application permit prolonged storage of a biological sample comprising nucleic acids (e.g., RNA, DNA) in a dry format under ambient conditions. In a further aspect of the invention, a dry solid matrix for ambient extraction and storage of nucleic acids (e.g., RNA, DNA) from a sample comprises a thiocyanate salt, a reducing agent, a buffer, and optionally a free-radical trap or RNase inhibitor present in a solid matrix in a dried format. In another embodiment, a dry solid matrix for extraction and storage of nucleic acids (e.g., RNA, DNA) from a sample comprises at least one metal thiocyanate salt, wherein at least one metal thiocyanate salt is not guanidinium thiocyanate (GuSCN), a reducing agent, a buffer, and optionally a free-radical trap or RNase inhibitor.

Nucleic acids (e.g., RNA, DNA) stored in a ambient state on dry solid matrices may be subjected to a process to release the nucleic acids from the solid matrix in an intact format that is suitable for further analyses of the collected nucleic acid samples. Methods of using the solid matrices of the invention for extracting and storing nucleic acids from a biological sample are also provided.

DRAWINGS

These and other features, aspects, and advantages of the chemically modified porous membranes will become better understood when the following detailed description is read with reference to the accompanying drawings in which like characters represent like parts throughout the drawings, wherein:

FIG. 3 provides gel pixel intensities for 28s and 18s rRNA for each of the depicted compositions. Cellulose substrates were stored for 13 days at room temperature in a desiccator cabinet prior to analysis. The ratio of 28s to 18s rRNA for each of the experimental conditions appears above each bar on the graph. Additional experimental details are set forth in the Example section below.

FIG. 4 provides gel pixel intensities for 28s and 18s rRNA for each of the depicted compositions. Cellulose samples were stored for 10 days at room temperature in a desiccator cabinet prior to analysis. The ratio of 28s to 18s rRNA for each of the experimental conditions appears above each bar on the graph. Additional experimental details are set forth in the Example section below.

FIG. 5 provides gel pixel intensities for 28s and 18s rRNA bands for each of the compositions shown. Cellulose samples were stored for 30 days at room temperature in a desiccator cabinet prior to analysis. The ratio of 28s to 18s rRNA for each of the experimental conditions appears above each bar on the graph. Additional experimental details are set forth in the Example section below.

FIG. 7 provides evidence for mRNA protection against sun damage on cellulose substrates. Each bar in the graph represents the difference in qRT-PCR cycle thresholds between UV-treated and untreated samples comprising the indicated compositions in the figure. Additional experimental details are set forth in the Example section below.

DETAILED DESCRIPTION

Dry solid matrices for ambient extraction and storage of nucleic acids (e.g., RNA, DNA, or a combination thereof) from a sample (e.g., a biological sample), wherein a composition comprising a protein denaturant, a reducing agent, a buffer, and optionally a free-radical trap or RNase inhibitor is incorporated into the solid matrix in a dry state, are described herein. In a further embodiment disclosed herein, the solid substrates for extraction and dry storage of nucleic acids (e.g., RNA, DNA, or a combination thereof) under ambient conditions comprise at least one thiocyanate salt, wherein at least one thiocyanate salt is not guanidinium thiocyanate (GuSCN), a reducing agent, a buffer, and optionally a free-radical trap or RNase inhibitor present in a solid matrix in a dried format. "Incorporation" of the compositions described above includes but is not limited to the "dipping" procedure described below. One of skill in the art will appreciate that many such methods exist to accomplish incorporation of the composition into the dry solid matrix. Following incorporation of the composition into the dry solid matrix, the solid matrix is dried in accordance with any appropriate method.

The compositions of the invention permit prolonged dry preservation of nucleic acids from a sample under ambient storage conditions. This observation is of particular importance with regard to RNA, which is widely known to be unstable under ambient conditions. The term "solid matrix" as used herein includes but is not limited to cellulose-based products, cellulose, cellulose acetate, glass fibers, or any combination thereof. A solid matrix of the present application may be porous. In particular embodiments, the solid matrix is a porous cellulose paper from Whatman™, such as 903, 31-ETF, FTA™ or FTA™ Elute. The terms membrane, paper, cellulose paper, solid matrix, and substrate may be used interchangeably throughout this disclosure. One of skill in the art would immediately recognize these are used in the art to refer to the same type of composition.

The term "extraction" refers to any method for separating and isolating the nucleic acids from a sample, more particularly a biological sample. Nucleic acids such as RNA and DNA can be released, for example, during evaporative sample cell lysis in the air or by the presence of compounds in a chemically modified solid matrix that upon contact with the samples results in cell lysis and the release of nucleic acids (e.g., FTA™ Elute cellulose papers). One of skill in the art will appreciate that any method that results in the extraction of nucleic acids, particularly RNA, from a sample (e.g., an unpurified biological sample) such that the nucleic acids can be captured on the solid matrix for stabilization, and preservation of the nucleic acids may be used in the disclosed compositions and methods. The above examples of methods for the extraction of nucleic acids from a sample are provided for illustrative purposes only. The terms "storage" or "preservation" may be used interchangeably herein with respect to maintaining the extracted nucleic acids in a format suitable for further analysis.

Skilled artisans in the field of nucleic acids, particularly RNA, traditionally assess the stability and quality of RNA on the basis of: (1) quantitative RT-PCR amplification of mRNA targets; (2) RNA Integrity Number (RIN) analysis on an Agilent 2100 Bioanalyzer; and (3) the ratio of 28s:18s ribosomal RNA (rRNA), which compromises the bulk of total cellular RNA. High-quality cellular RNA generally exhibits a 28s:18s rRNA ratio greater than 1 and a RIN score approaching 10. In practice, a desirable RIN score is generally greater than 5. Moreover, high-quality cellular RNA supports efficient amplification of both low-abundance and large (e.g., great thanl kB) mRNAs. For the purposes of convenience, rRNA signal intensity and the ratio of 28s:18s rRNA are frequently used to rapidly screen and identify samples with robust RNA storage properties by gel electrophoresis.

As defined herein, a "biological sample" includes but is not limited to blood, serum, tissue, nasal mucous, and saliva obtained from any organism, including a human. Biological samples may be obtained by an individual undergoing a self-diagnostic test (e.g., blood glucose monitoring) or by a trained medical professional through a variety of techniques including, for example, aspirating blood using a needle or scraping or swabbing a particular area, such as a lesion on a patient's skin Methods for collecting various biological samples are well known in the art. The term "sample" includes biological samples as defined above, but also includes, for example, tissue cultured cells and purified nucleic acids.

A composition comprising a protein denaturant, a reducing agent, and a buffer is present in the dry solid matrix of this disclosure. The composition may comprise one or more of each of the above-listed components. The composition may optionally further comprise an ultraviolet (UV) inhibitor, a free-radical trap, an RNase inhibitor, a chelator, or any combination thereof. The skilled artisan will appreciate that numerous protein denaturants are known in the art and can be empirically selected for use in the compositions and methods described here. Without intending to be limited to a particular protein denaturant, exemplary protein denaturants include guanidinium thiocyanate, guanidinium hydrochloride, arginine, sodium dodecyl sulfate (SDS), urea, or any combination thereof. A schematic of an exemplary protein denaturant is set forth below:

Wherein each R may be independently a member selected from the group consisting of hydrogen, a heteroatom containing radical or a hydrocarbon radical.

The heteroatom containing radical is a group comprising a member or members selected from nitrogen, oxygen, sulfur, phosphorus, silicon, and boron. It is an object to bind a guanidine containing compound using reactive functional groups. Typical reactive groups which bear heteroatoms include epoxy, acrylate, maleimide, acyl halide, alkyl halide, azide, cyanate ester, isocyanate, aryl halide, aldehyde, amine, oxime, thiol, alcohol, acid, aziridine, azo, Isothiocyanate, anhydride, mixed anhydride, lactone, sultone, and ketone.

The hydrocarbon radical is a group comprising both carbon and hydrogen, though may also contain heteroatoms to enhance hydrophilicity. It is an object to bind a guanidine containing compound using reactive functional groups. Typical reactive groups which bear hydrocarbon include allyl, styryl, vinyl, and alkyne. Heteroatom containing hydrocarbon groups include 2, 3 or 4-oxystyryl, aminoallyl, oxyallyl, oxyvinyl, amino vinyl.

X is an anion, which is a radical containing one or more formal negative charge(s). A member or members selected from the group consisting of chloride, thiocyanate, sulfate, phosphate, bromide, chlorite, chlorate, thiosulfate, carbonate, hydrogen carbonate, acetate, formate, hydrogen phosphate, dihydrogen phosphate. It is envisioned that on or more anions may be used in and combinations of anions bearing various levels (divalent, monovalent, trivalent) of formal charge may be used. The molecular weight of the anion may vary from 10-100,000.

The term "reducing agent" refers to a chemical species that provides electrons to another chemical species. Again, a variety of reducing agents are known in the art, and the exemplary list provided below and in the claims is in no way intended to limit the reducing agent(s) that could be used in the compositions and methods of the present disclosure. Exemplary reducing agents include dithiothreitol (DTT), 2-mercaptoethanol (2-ME), and tris(2-carboxyethyl)phosphine (TCEP) and their related salts (e.g., TCEP-hydrochloride). Moreover, any combination of these or other reducing agents may be used to practice the invention. In particular embodiments, the reducing agent is TCEP. In particular embodiments, the TCEP can be added as its hydrochloride salt, TCEP-HCl.

"Buffer" as used herein includes, for example, 2-Amino-2-hydroxymethyl-propane-1,3-diol (Tris), 2-(N-morpholino) ethanesulfonic acid (MES), 3-(N-morpholino)propane- sulfonic acid (MOPS), citrate buffers, 4-(2-hydroxyethyl)-1-piperazineethanesulfonic acid (HEPES), and phosphate buffers. This list of potential buffers is for illustrative purposes only. The skilled artisan would recognize that the pH of the buffer selected for use in the compositions and methods disclosed herein is relevant. The pH of the buffer will typically be in the range of 3 to 8.

As indicated above, the composition present in the solid matrix may optionally comprise a UV protectant or a free-radical trap. In certain aspects of the invention, a UV protectant or a free-radical is required in the composition of the incorporated in the dry solid matrix for the extraction and storage of nucleic acids. Without intending to be limited to any specific UV protectant, exemplary agents include, for example, hydroquinone monomethyl ether (MEHQ), hydroquinone (HQ), toluhydroquinone (THQ), and ascorbic acid or vitamin C. In certain aspects, the free-radical trap is MEHQ or THQ. The terms "UV protectant" or "free radical trap" may be used interchangeably herein with respect to maintaining the extracted nucleic acids in an unmodified state for further analysis. The composition in the solid matrix may also include RNase inhibitors such as vanadyl ribonucleoside complex (VRC) or any of the commercially available RNase inhibitors (e.g., SUPERase-In™). Additional exemplary RNase inhibitors are described in Kumar et al. (2003) *Biochemical and Biophysical Research Communications* 300: 81-86, which is herein incorporated by reference in its entirety.

Methods of using the compositions described herein above are further provided. In one embodiment, a method for extracting and preserving nucleic acids (e.g., RNA, DNA, or a combination thereof) comprises the steps of: a) providing a solid matrix, wherein a composition comprising at least one protein denaturant, at least one reducing agent, a biological buffer, and optionally a free-radical trap or RNase inhibitor is incorporated into the solid matrix in a dried format; b) applying a sample (e.g., a biological sample) to the solid matrix to extract the nucleic acids; c) drying the solid matrix; and d) storing the nucleic acids on the solid matrix in a dry state under ambient conditions. In certain aspects of the method, the solid matrix is a porous cellulose-based paper such as the commercially available 903, 31-ETF, or FTA Elute™. Performance of this method permits the storage of nucleic acids, particularly RNA which is widely known to be an unstable biomolecule to store, in a dry format (e.g., on a solid matrix) under ambient temperatures. The samples utilized in this method include but are not limited to biological samples such as blood, serum, tissue, nasal mucous, and saliva obtained from any organism, including a human.

The method delineated above may optionally include a step to recover the nucleic acids from the solid matrix for further analysis. For example, the nucleic acids may be recovered by rehydrating the solid matrix (e.g., cellulose paper) in an aqueous solution, a buffer solution, as defined above, or an organic solution. Alternatively, the nucleic acids could be recovered from the solid matrix by electroelution. One of skill in the art will appreciate that any method capable of recovering the nucleic acids from the solid matrix may be used to practice the disclosed methods.

In a further aspect of the invention, the method for extracting and storing nucleic acids from a sample comprising the steps of: a) providing a dry solid matrix, wherein a composition comprising at least one thiocyanate salt, wherein the at least one thiocyanate salt is not guanidinium thiocyanate (GuSCN), at least one reducing agent, a buffer, and optionally a free-radical trap or RNase inhibitor is incorporated into the solid matrix and the solid matrix is dried; b) applying a sample (e.g., a biological sample) to the solid matrix to extract the nucleic acids; c) drying the solid matrix; and d) storing the nucleic acids on the solid matrix in a dry state under ambient conditions. Another embodiment of the invention is a method for extracting and storing nucleic acids from a sample comprising the steps of: a) providing a dry solid matrix, wherein a composition comprising at least one metal thiocyanate salt, wherein the composition does not contain guanidinium thiocyanate (GuSCN), at least one reducing agent, a buffer, and optionally a free-radical trap or RNase inhibitor is incorporated into the solid matrix and the solid matrix is dried; b) applying a sample (e.g., a biological sample) to the solid matrix to extract the nucleic acids; c) drying the solid matrix; and d) storing the nucleic acids on the solid matrix in a dry state under ambient conditions. In certain aspects, the metal thiocyanate salt comprises a Group 1 or Group 2 metal cation, and the metal thiocyanate salt includes but is not limited to sodium thiocyanate, potassium thiocyanate, magnesium thiocyanate, calcium thiocyanate, barium thiocyanate, and zinc thiocyanate.

In certain aspects of the method, the solid matrix is a porous cellulose-based paper such as the commercially available 903, 31-ETF, or FTA Elute™ Performance of this method permits the storage of nucleic acids, particularly RNA which is widely known to be an unstable biomolecule to store, in a dry format (e.g., on a solid matrix) under ambient temperatures. The samples utilized in this method include but are not limited to biological samples such as blood, serum, tissue, nasal mucus, and saliva obtained from any organism, including a human.

The term "nucleic acid" refers to all forms of RNA (e.g., mRNA, miRNA, rRNA, tRNA, piRNA, ncRNA), DNA (e.g. genomic DNA, mtDNA), as well as recombinant RNA and DNA molecules or analogues of DNA or RNA generated using nucleotide analogues. The nucleic acid molecules can be single stranded or double stranded. Strands can include the coding or non-coding strand. Fragments of nucleic acids of naturally occurring RNA or DNA molecules are encompassed by the present invention and may be recovered using the compositions and methods disclosed. "Fragment" refers to a portion of the nucleic acid (e.g., RNA or DNA).

The following examples are offered by way of illustration and not by way of limitation:

EXAMPLES

Example 1

General RNA Analysis

A cultured human lymphocyte cell line (i.e., Jurkat cells) was utilized as the source of total cellular RNA. Cells were dried on 7-mm cellulose discs impregnated with the indicated reagents, stored at room temperature for 10 days in a desiccator cabinet, and cellular nucleic acids were electroeluted in accordance with standard protocols. Briefly, discs were rehydrated with 15 µL of 2 mg/mL proteinase K in nuclease-free water to remove excess protein and dried for ~30 min. Punches were placed into individual wells of a 1% Trisborate-EDTA (TBE) agarose gel and suspended inlX Gel Loading Buffer II containing formamide (Ambion). Cellular nucleic acids were electrophoresed at 110 volts for 1-2 hours, and RNA and DNA were post-stained with SYBR Gold (Invitrogen) and detected using a Typhoon Imager (GE Healthcare). All equipment and surfaces were treated with RNAZap (Ambion) to preserve the integrity of cellular RNA during and subsequent to electro-elution from cellulose. Internal standards, including RNA 6000 Nano Ladder (Agilent Technologies) and purified human total RNA from muscle (Origene), were included on agarose gels to both monitor RNase contamination and identify control rRNA bands.

Electrophoretograms were digitally quantified using ImageJ software. Briefly, a vertical line was drawn from the top to the bottom of each gel lane, and pixel intensity (in gray value arbitrary units) was plotted as function of line distance (cm) using the Plot Profile function. Peaks corresponding to genomic DNA and 28s/18s rRNA were identified and used to calculate the ratio of 28s:18s rRNA.

Figure 1:
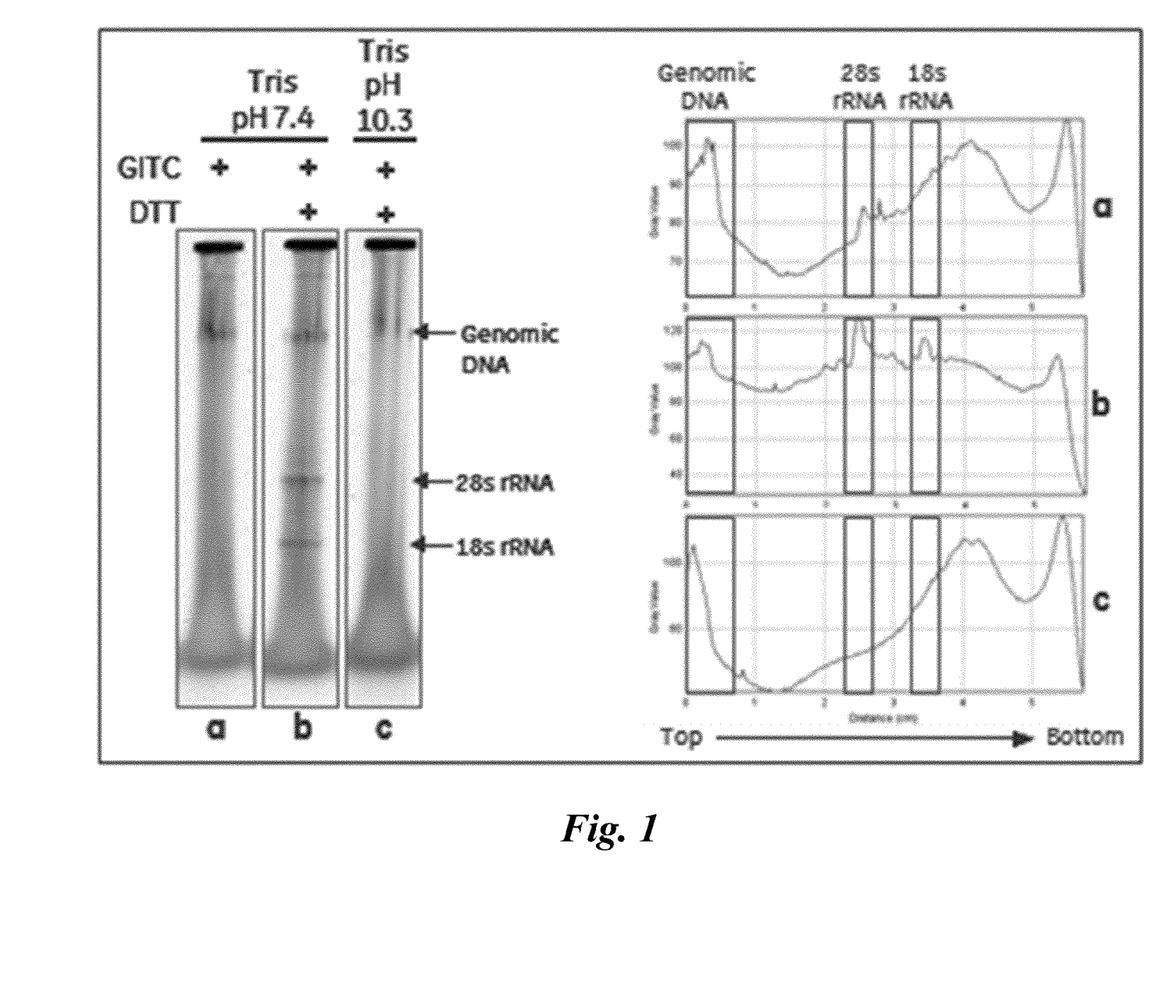
FIG. 1 provides a representative electrophoretogram of nucleic acids recovered from cellulose through electro-elution after spotting cultured human cells onto solid matrices of different compositions. High molecular weight genomic DNA and 28s/18s rRNA bands are indicated. Quantitation of DNA and RNA using Image J is further provided. A vertical line was drawn from the top of each gel lane to the bottom in panel A, and pixel intensity (gray value arbitrary units) was plotted as function of line distance (cm) using the Plot Profile function. Peaks corresponding to genomic DNA and 28s/18s rRNA are shown in the boxes. Additional experimental details are set forth in the Example section below.

FIG. 1 provides a representative electrophoretogram of nucleic acids recovered from cellulose using electroelution. High molecular weight genomic DNA and 28s/18s rRNA bands are indicated.

FIG. 1 further provides quantitation of DNA and RNA using Image J. A vertical line was drawn from the top of each lane to the bottom in panel A, and pixel intensity (gray value arbitrary units) was plotted as function of line distance (cm) using the Plot Profile function. Peaks corresponding to genomic DNA and 28s/18s rRNA are "boxed."

Example 2

Empirical Determination of Favorable Conditions for RNA Extraction and Storage

The primary purpose of this example was to evaluate the effect of each single factor and the effect of the combination of factors tested (e.g., chelating agent, buffer, pH, protein denaturant, reducing agent, and peptide RNase inhibitor) on preserving RNA on cellulose paper. An additional aspect of this example was to evaluate the presence of reducing agent (DTT) to potentially enhance the effect of the protein denaturant.

Jurkat cells were again utilized as the source of total cellular RNA, and the cells were applied directly onto cellulose paper samples and air-dried to mimic a typical end-user application. Total cellular RNA was recovered by electroelution, following the protocol described above in Example 1, into a 1% agarose gel and analyzed for 28s:18s rRNA content based on known standards. Samples containing the components listed under each bar on the graph of FIG. 2 were stored for 10 days at room temperature in a desiccator cabinet prior to analysis.

Figure 2:
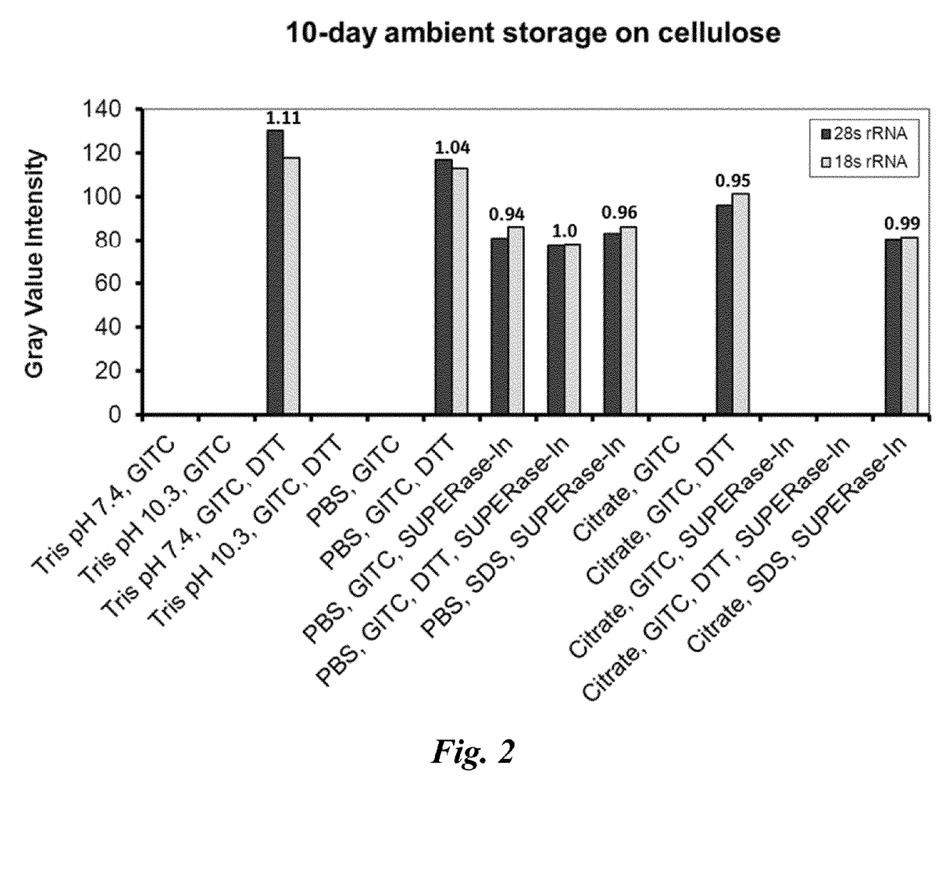
FIG. 2 provides gel pixel intensities, presented as gray value arbitrary units, for 28s and 18s rRNA for each of the depicted compositions. Cellulose samples were stored for 10 days at room temperature in a desiccator cabinet prior to analysis. The ratio of 28s to 18s rRNA is set forth above each bar on the graph. Additional experimental details are set forth in the Example section below.

The results of Example 2 are set forth in FIG. 2. Numbers above each bar correspond to the ratio of 28s to 18s rRNA. A 28s:18s ratio >1 generally indicates intact RNA. Several compositions failed to stabilize rRNA, including samples lacking reducing agent (DTT) or SUPERase-In to inactivate RNase, or samples possessing an alkaline pH. Samples containing GITC, DTT, and neutral buffer outperformed all other tested reagent combinations.

Example 3

Continued Empirical Determination of Favorable Conditions for RNA Extraction and Storage After key components for storing RNA were identified in Example 2, Example 3 was designed to investigate the effect of DTT and SDS either alone or in combination on the ability to preserve RNA, and the effect of a free radical trap and chelating agent on the performance of GITC/DTT combinations that exhibited favorable RNA stabilization properties in Example 2.

Jurkat cells were applied directly onto cellulose paper samples and air-dried to mimic a typical end-user application. Total cellular RNA was recovered by electroelution, following the protocol described above in Example 1, into a 1% agarose gel and analyzed for 28s:18s rRNA content based on known standards.

Figure 3:
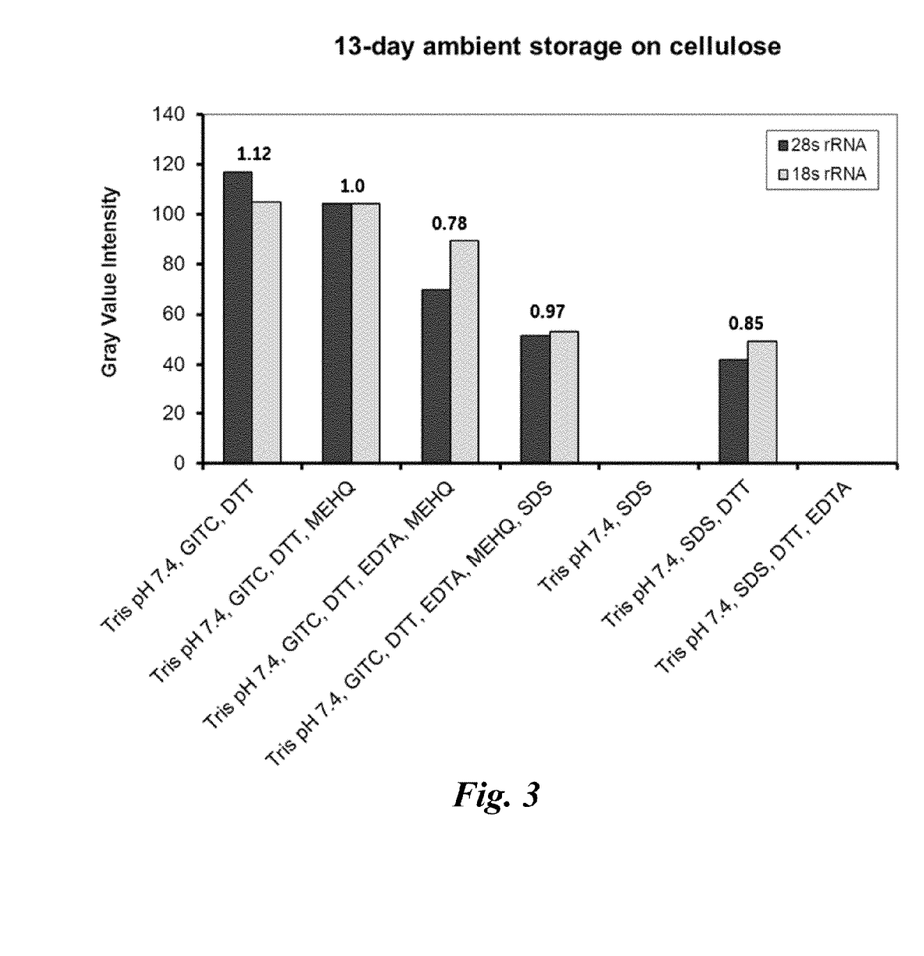

Cellulose samples were stored for 13 days at room temperature in a desiccator cabinet prior to analysis. Numbers above each bar correspond to the ratio of 28s to 18s rRNA. A 28s:18s ratio >1 generally indicates intact RNA. The results of Example 3 are provided in FIG. 3. GITC/DTT combinations generally exhibited better RNA stabilization properties than SDS/DTT combinations. Supplementing either combination with a chelating agent (EDTA) resulted in comparatively poorer RNA quality.

Example 4

Continued Empirical Determination of Favorable Conditions for RNA Extraction and Storage After additional key components for storing RNA were identified in Example 3, Example 4 was designed to investigate if an alternative reducing agent (TCEP), which has better stability and much less odor, could be substituted for DTT. Another factor introduced into this example was vanadyl ribonucleoside complex (VRC), a small molecule RNase inhibitor. These substitutions were compared and evaluated for the ability to stabilize rRNA.

Figure 4:
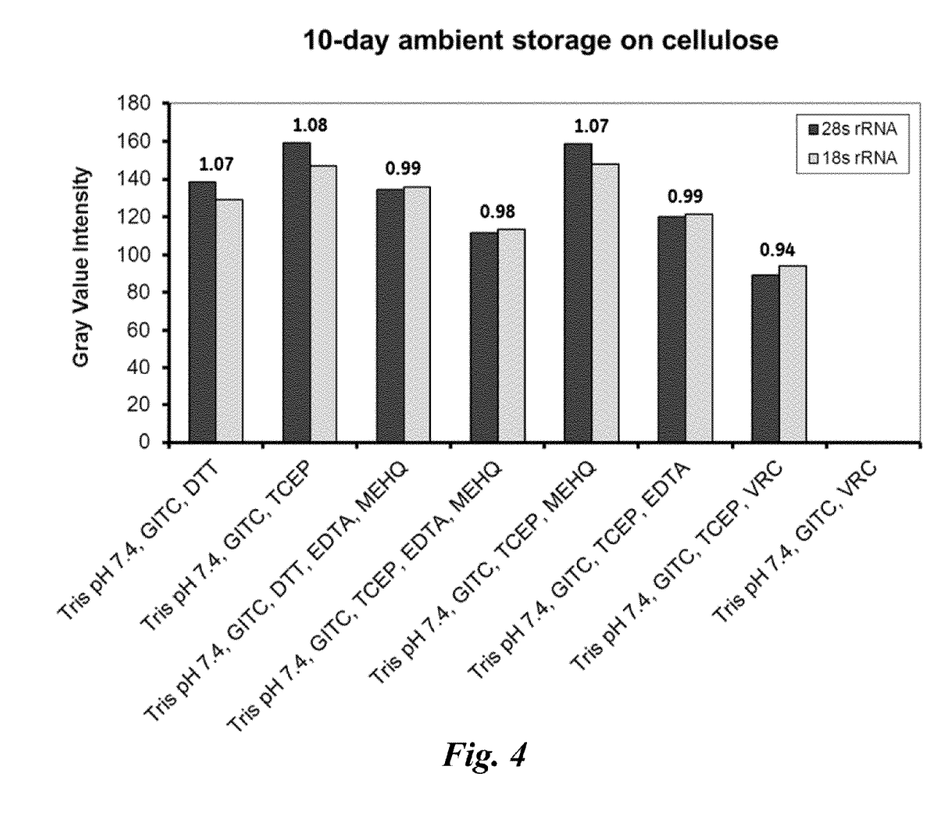

Jurkat cells were applied directly onto cellulose paper samples and air-dried to mimic a typical end-user application. Total cellular RNA was recovered by electroelution, following the protocol described above in Example 1, into a 1% agarose gel and analyzed for 28s:18s rRNA content based on known standards. Cellulose samples were stored for 10 days at room temperature in a desiccator cabinet prior to analysis. Numbers above each bar correspond to the ratio of 28s to 18s rRNA. A 28s:18s ratio >1 generally indicates intact RNA. The results of Example 4 are provided in FIG. 4. TCEP and DTT can be used interchangeably to stabilize RNA in several substrate compositions.

Example 5

Long-Term Performance of Select Compositions for RNA Storage on Cellulose

Figure 5:
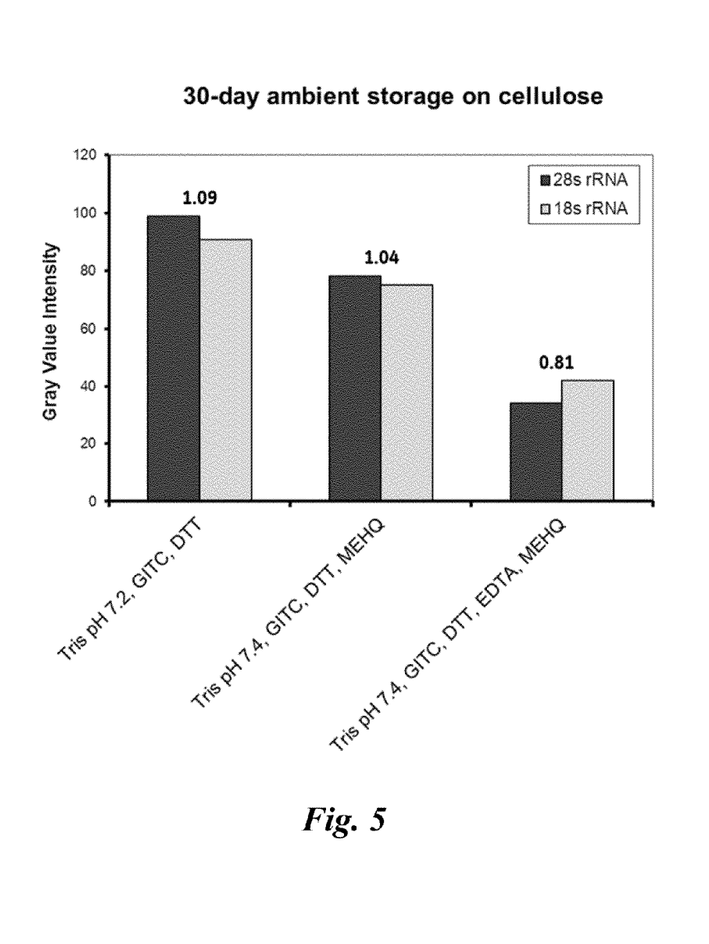

Example 5 was designed to evaluate the long-term performance of select compositions after 30 days of room temperature storage. Jurkat cells were applied directly onto cellulose paper samples and air-dried to mimic a typical end-user application. Total cellular RNA was recovered by electroelution, following the protocol described above in Example 1, into a 1% agarose gel and analyzed for 28s:18s rRNA content based on known standards. Cellulose samples were stored for 30 days at room temperature in a desiccator cabinet prior to analysis. Numbers above each bar correspond to the ratio of 28s to 18s rRNA. A 28s:18s ratio >1 generally indicates intact RNA. The results of Example 5 are set forth in FIG. 5.

Example 6

Stability Analysis of RNA in Dried Blood Spots

Figure 6:
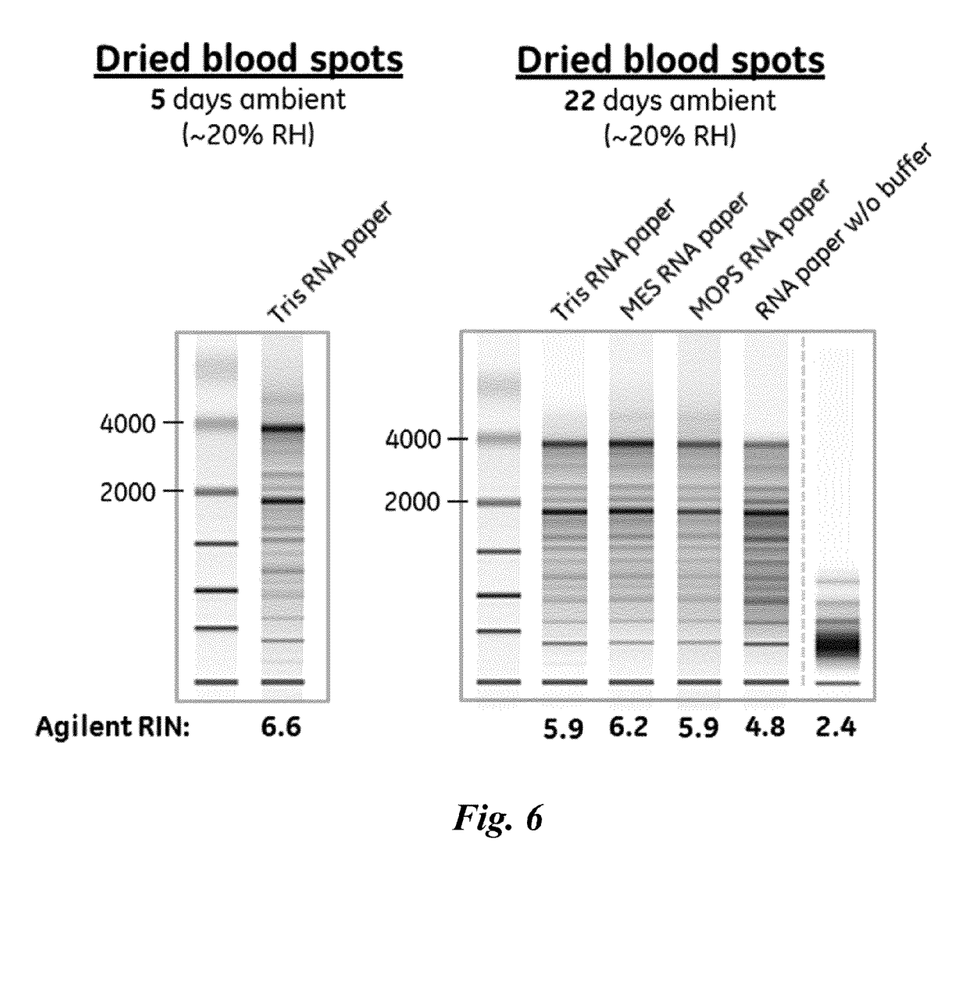
FIG. 6 provides RNA Integrity Numbers (RIN) measured from dried blood spots on cellulose substrates, as determined on an Agilent 2100 Bioanalyzer using RNA 6000 Pico Lab-Chips, for each of the conditions listed. Additional experimental details are set forth in the Example section below.

Example 6 was designed to evaluate the performance of a select RNA-stabilizing paper composition (GITC/TCEP/MEHQ) with fresh whole blood at a variety of buffer conditions. Approximately 50 µL of rat whole blood was collected from the tail vein of a test subject and spotted onto FTA paper or RNA-stabilizing paper prepared with the indicated buffer components. Cards were dried and stored at ambient temperature but controlled humidity (~20% relative humidity) for 5 to 22 days. RNA was extracted from a 7 mm center punch into lysis buffer and purified through a silica-membrane spin column in accordance with protocols known in the art. Following purification and elution, RNA Integrity Numbers (RIN) were measured on an Agilent 2100 Bioanalyzer using RNA 6000 Pico LabChips. By convention, RIN >5 are good but RIN >6 are best for quantitative downstream analyses such as RT-PCR or microarray applications. The results of Example 6 are presented in FIG. 6. Overall RNA quality from this select paper composition (GITC/TCEP/MEHQ) at all tested buffer compositions exceeded the performance of FTA paper.

Example 7

Impact of UV Protection on RNA Stability

Figure 7:
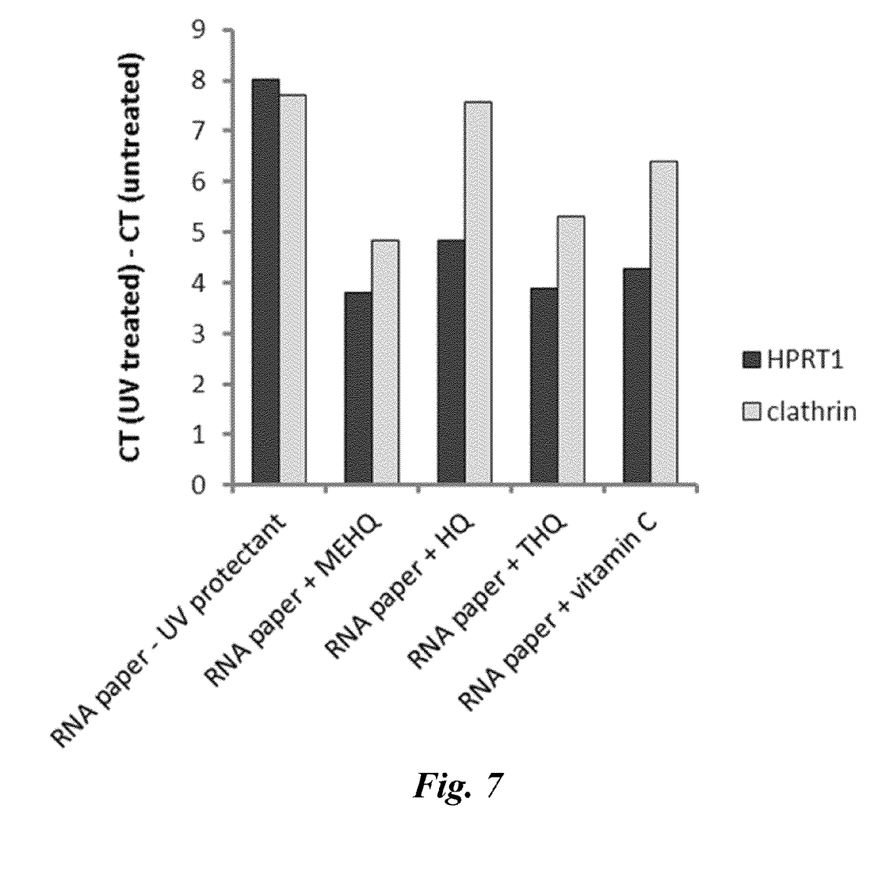

Example 7 was designed to demonstrate mRNA protection by UV inhibitors and free radical traps present in a select dry matrix (GITC/TCEP/Tris). DNA-free total Jurkat RNA (1 µg) was spotted in duplicate onto RNA-stabilizing paper containing the indicated components. Each card was split and one half was kept in the dark at 35° C. for 20 hours, while the other was treated in a Q-SUN Xe-1 Xenon test chamber for 20 hours (35° C., 0.3 W/cm$^2$, 340 nm) to replicate the full energy spectrum of sunlight (21.7 kJ/m$^2$ total energy). A 1.2 mm punch was taken from each sample and dropped directly into reverse-transcriptase reactions to create a cDNA library, which was then probed against primers specific to HPRT1 and clathrin mRNA by qPCR. Cycle thresholds ($C_T$) for samples exposed to UV were subtracted from the $C_T$ of untreated mate-pairs stored in the dark. The results of Example 7 are presented in FIG. 7. Vitamin C is used synonymously in the figure for ascorbic acid.

Example 8

Stability of Reducing Agent on Paper Under Ambient Conditions

31ETF cellulose-based paper from Whatman™ was immersed in increasing concentrations of TCEP or DTT in the presence of GITC in Tris buffer, pH 7.4. The cellulose based papers were stored at room temperature without humidity regulation. At the days 5, 19, and 105, 5,5'-Dithiobis(2-nitrobenzoic acid) ("DTNB") was placed on each paper sample. In the presence of an active reducing agent, an instant color change to yellow was observed. Up to 105 days of storage under ambient conditions, the cellulose paper coated the TCEP solution, at all concentrations, was still active and able to reduce DTNB as indicated by a visible change in color of the paper from white to yellow. The paper samples immersed in DTT were not able to reduce DTNB, and, accordingly, the color of the paper remained white. These figures do not convey their meaning in black and white and, as such, have not been included herein but are available at the Examiner's request. The chemical reaction relevant to the reduction of DTNB is provided in Cline et al. (2004) *Biochemistry* 43: 15195-15203.

Example 9

Qualitative Analysis of Aging of Reducing Agents

31-ETF cellulose paper samples contained GITC in Tris buffer, pH 7.4, with different concentrations of the reducing agents TCEP or DTT. The paper samples were stored under the following different conditions: 1) 21° C., 10% relative humidity; 2) 21° C., 80% relative humidity; and 3) 41° C., 10% relative humidity.

At day 0, 1, 6, and 25, a 10 mg sample of cellulose paper under each condition were put into a DTNB solution, shaken briefly, and color images were taken. At day 1, all of the TCEP samples under each of the environmental conditions were able to change color of the DTNB solution to yellow, indicating it was still able to function as a reducing agent. In contrast, DTT failed to turn the samples yellow in the presence of DTNB, even at 21° C. and 10% relative humidity. At day 25, TCEP paper stored at 21° C. and 10% relative humidity continued to show functional reducing activity. An increase of either the humidity or the temperature, however, resulted in a noticeable decrease in TCEP activity as a reducing agent, indicating that both temperature and humidity are relevant factors in TCEP function as a reducing agent.

Example 10

Qualitative Analysis of TCEP Activity on Cellulose-Based Paper

TCEP compositions further comprising GITC and MEHQ in different buffers (Tris, pH 7.4; MES, pH 6.2; and MOPS, pH 7.0) and a control sample comprising no buffer were prepared. Cellulose-based paper was then coated, each with a different one of the above solutions, fast dried at 50° C. in an oven with air blow, sealed with desiccants in aluminum foil bags to keep moisture low, and then stored at 4° C., room temperature, or 41° C.

Figure 8:
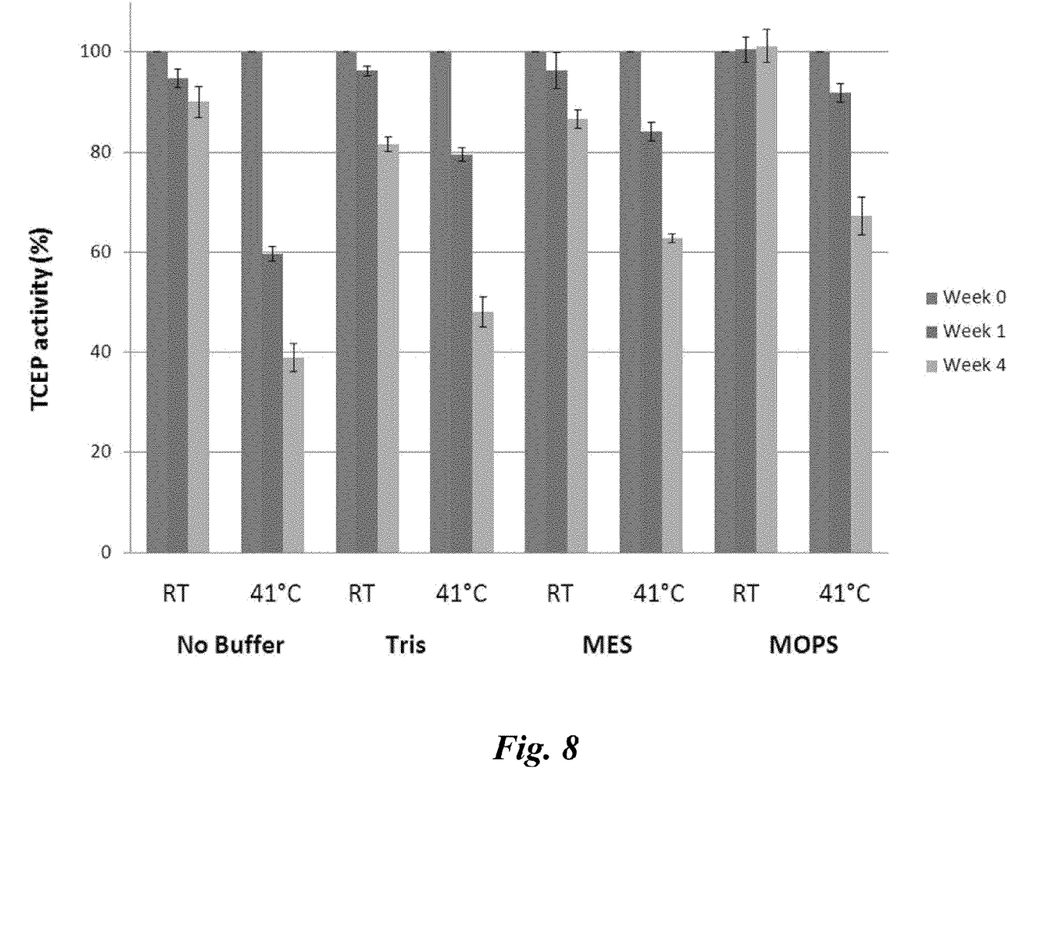
FIG. 8 provides TCEP activity on cellulose-based papers in the presence of different buffers and at different temperatures over a 4-week time period. Additional details are provided in the Example section.

At the weeks indicated in the FIGS. 0, 1, and 4), TCEP activity was analyzed using a DTNB colorimetric assay in which DTNB was added to each 3.6 mm paper punch, was stirred for 30 minutes, and then the absorbance of the liquid at 412 nm was measured.

All samples were stable at 4° C. with approximately 100% activity at one month. Following one month at room temperature, TCEP activity displayed variability based on the buffer utilized (e.g., MOPS (100%)>No buffer (90%)>MES (86%) >Tris (81%)). After one month at 41° C., variability in TCEP activity was still observed (e.g., MOPS (67%)>MES (63%) >Tris (48%)>No buffer (39%)). Overall, TCEP reducing power on cellulose was highest in the presence of MOPS buffer under the tested environmental conditions.

Example 11

Conditions for Robust Substrate Preparation, Dry Storage at Ambient Temperature, and RNA Extraction and Analysis A cultured human lymphocyte cell line, more particularly the Jurkat cell line, was utilized to provide a sample of total cellular RNA. The cells were spotted onto 7-mm cellulose discs impregnated with the reagents indicated in the table below at the specified concentrations. The discs containing the reagents set forth below were prepared via a "dipping" protocol in which pieces (~4 in$^2$) of cellulose paper (Whatman™ 31-ETF paper) were saturated by placing the Whatman™ 31-ETF paper in petri dishes of the dipping solutions containing the amounts of the reagents listed in Table 1. The dipping solutions were prepared by adding deionized water to the indicated thiocyanate salt (e.g., NaSCN, KSCN, NH$_4$SCN, Ca(SCN)$_2$, Mg(SCN)$_2$, Ba(SCN)$_2$, Co(SCN)$_2$, Zn(SCN)$_2$, or NaClO$_4$) MOPS, TCEP-HCl, and MEHQ or THQ to achieve the desired concentrations of each of these reagents in the dipping solutions. The dipping solutions were agitated on a vortex to ensure complete dissolution of the solid reagents, and the pH of each of the final dipping solutions was determined in accordance with methods known in the art.

TABLE 1

Concentrations of Reagents in Dip Coating Solutions

| Salt | [-SCN] (mM) | [TCEP-HCl] (mM) | [MOPS] (mM) | [MEHQ] (mM) | [THQ] (mM) | pH |
|---|---|---|---|---|---|---|
| NaSCN | 420 | 35 | 96 | 40 | 0 | 2.0 |
| NaSCN | 420 | 35 | 88 | 40 | 0 | 4.5 |
| NaSCN | 420 | 35 | 88 | 40 | 0 | 7.0 |
| NaSCN | 308 | 35 | 88 | 40 | 0 | 4.6 |
| NaSCN | 208 | 35 | 88 | 40 | 0 | 4.3 |
| NaSCN | 104 | 35 | 88 | 40 | 0 | 5.0 |
| KSCN | 420 | 35 | 88 | 40 | 0 | 4.5 |
| NH$_4$SCN | 420 | 35 | 88 | 40 | 0 | 4.5 |
| Ca(SCN)$_2$ | 424 | 35 | 96 | 0 | 40 | 3.3 |
| Mg(SCN)$_2$ | 424 | 35 | 96 | 0 | 40 | 3.3 |
| Ba(SCN)$_2$ | 424 | 35 | 96 | 0 | 40 | 3.3 |
| Co(SCN)$_2$ | 424 | 35 | 96 | 0 | 40 | 3.2 |
| Zn(SCN)$_2$ | 424 | 35 | 96 | 0 | 40 | 3.2 |
| NaClO$_4$ | 424 | 35 | 96 | 0 | 40 | 3.2 |

Once the cellulose paper was saturated, the excess solution was removed with a nip roller and the paper was dried at 50° C. under a stream of N$_2$ gas. Jurkat cells (e.g., source of total cellular RNA) were applied to the dried paper substrate comprising the combination of reagents as set forth in Table 1. The cellulose substrates comprising the total cellular RNA from the Jurkat cells along with the reagents as in the above table were dried and stored at room temperature for 7-17 days in a desiccator cabinet maintained at ~20% relative humidity (RH).

Cellular RNA was extracted from each cellulose sample and measured in accordance with standard protocols. Briefly, cellulose samples were re-hydrated with 15 μL of 4 mg/mL proteinase K and cellular RNA was extracted from the cellulose matrix into lysis buffer and purified on silica-membrane spin columns in accordance with protocols known in the art. Following purification and elution into nuclease-free water, RNA Integrity Numbers (RIN) were measured on an Agilent 2100 Bioanalyzer using RNA 6000 Pico LabChips. By convention, RIN >5 are considered good but RIN >6 are considered preferable for quantitative downstream analyses such as RT-PCR or microarray applications.

Figure 9:
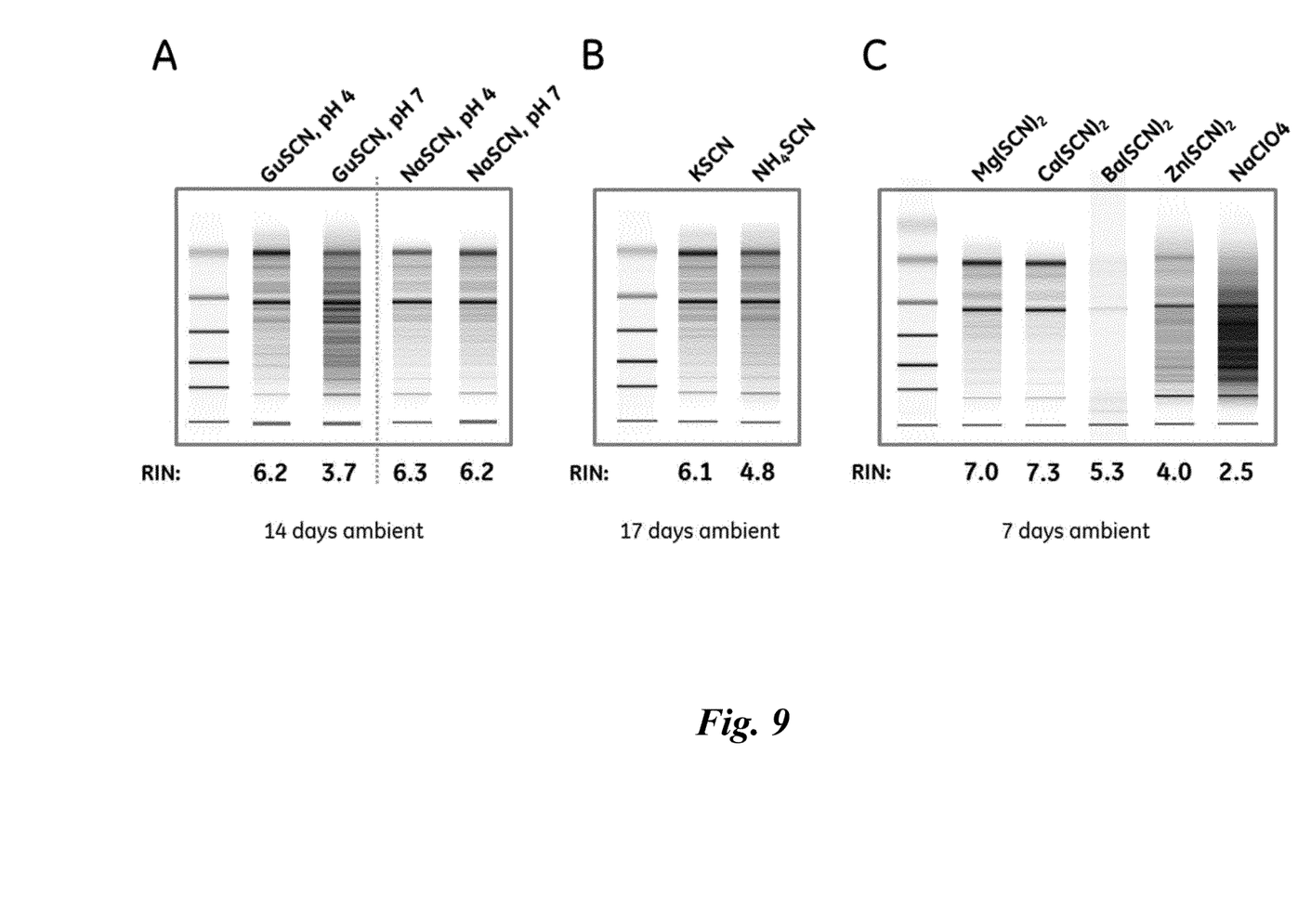
FIG. 9 provides RNA Integrity Numbers (RIN) for cultured human cells spotted onto chemically-impregnated cellulose substrates. Samples were stored at ambient temperature for at least a week prior to RNA analysis on an Agilent 2100 Bioanalyzer. Additional experimental details are set forth in the Examples section below.

The results of Example 11 are set forth in FIG. 9. It was observed that NaSCN can be directly substituted for GuSCN to extract and stabilize cellular RNA at ambient temperature. Unlike the case for GuSCN, this phenomenon was independent of the final solution pH used to impregnate the cellulose paper (pH 4 or pH 7). Because GuSCN contains a guanidinium cation that acts as a weak base at neutral pH, it is hypothesized that GuSCN may elicit alkaline hydrolysis of RNA at pH 7. Strong RNA stabilization properties were also observed for related thiocyanate salts containing metal or ammonium cations, but not for a perchlorate salt commonly used to extract nucleic acids. Of these related inorganic salts, thiocyanate salts with Group 1 or Group 2 metal cations (e.g., Na$^+$, K$^+$, Mg$^{+2}$, Ca$^{+2}$, Ba$^{+2}$) proved most effective in stabilizing RNA (RIN >5). One of skill in the art would appreciate that metal cations, especially divalent cations, are stimulatory cofactors for RNase enzymes and catalytic RNAs (e.g., ribozymes). Therefore, the applicability of Mg$^{2+}$- or Ca$^{2+}$-

Example 12

RNA Stability Analysis of Dried Blood Spots

Example 12 was designed to evaluate the performance of three different inorganic salts for stabilizing total cellular RNA from whole blood. Approximately 50 μL of rat whole blood was collected from the tail vein of a test subject and spotted onto chemically-treated paper containing the indicated salts at equimolar concentrations in combination with a reducing agent (e.g., TCEP), a buffer (e.g., Tris), and an antioxidant (e.g., THQ) in a dry format. The chemically treated dried cellulose papers were prepared essentially as described above in Example 11. Blood spots on the chemically-impregnated cellulose papers were dried and stored at ambient temperature at a controlled humidity of approximately 20% relative humidity for 19 days. RNA was extracted from a 7 mm center punch into lysis buffer and purified through silica-membrane spin columns in accordance with protocols known in the art. Following purification and elution, an RNA Integrity Number (RIN) was measured for each sample on an Agilent 2100 Bioanalyzer using RNA 6000 Pico LabChips. Again, an RIN >5 is considered good, but an RIN >6 are considered preferable for quantitative downstream analyses such as RT-PCR or microarray applications.

Figure 10:
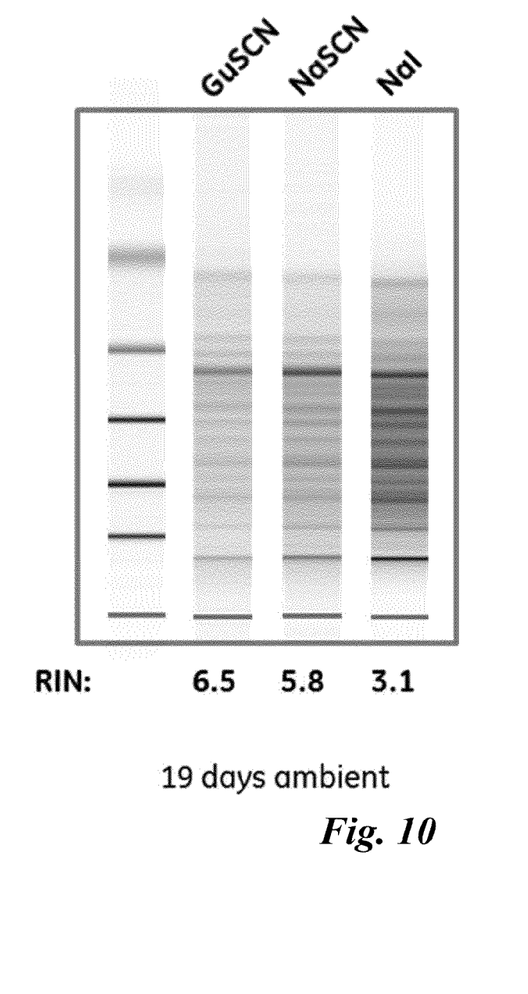
FIG. 10 provides RNA Integrity Numbers (RIN) for dried blood spots on chemically-impregnated cellulose substrates. Dried blood spots were stored at ambient temperature for 19 days prior to RNA analysis on an Agilent 2100 Bioanalyzer. Additional experimental details are set forth in the Examples section below.

The results of Example 12 are set forth in FIG. 10. The indicated thiocyanate salts impregnated in the cellulose paper substrates in Example 11 were essential equally effective in extracting and stabilizing RNA from rat blood at ambient temperature. On the basis of these results, the skilled artisan would appreciate any related thiocyanate salts may be used to practice the disclosed methods.

All publications, patent publications, and patents are herein incorporated by reference to the same extent as if each individual publication or patent was specifically and individually indicated to be incorporated by reference. The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

The invention claimed is:

1. A dry solid matrix for extraction and storage of nucleic acids from a biological sample, wherein a composition comprising;
   a metal thiocyanate comprises a Group 1 or Group 2 metal cation;
   a reducing agent where the reducing agent is tris(2-carboxyethyl)phosphine (TCEP); and
   a buffer; is incorporated into the dry solid matrix, and the matrix is then dried; and where the solid matrix is a porous matrix comprising cellulose, cellulose acetate, glass fiber, or any combination thereof.

2. The dry solid matrix of claim 1, wherein the Group 1 or Group 2 metal cation is selected from the group consisting of $Na^+$, $K^+$, $Li^+$, $Mg^{+2}$, $Ca^{+2}$, and $Ba^{+2}$.

3. The dry solid matrix of claim 1, wherein the composition present in the solid matrix further comprises a UV inhibitor, a free-radical trap, a chelator, or any combination thereof 4. The dry solid matrix of claim 1, wherein the composition incorporated into the dry solid matrix further comprises an RNase inhibitor.

5. The dry solid matrix of claim 1, wherein the dry solid matrix permits prolonged storage of nucleic acids in a dry format under ambient conditions.

6. The dry solid matrix of claim 5, wherein the nucleic acids are RNA, DNA, or a combination thereof.

7. The dry solid matrix of claim 6, wherein the nucleic acids are RNA.

8. The dry solid matrix of claim 1, wherein the porous matrix is a cellulose paper.

9. The dry solid matrix of claim 1, wherein the metal thiocyanate is selected from the group consisting of sodium thiocyanate, potassium thiocyanate, lithium thiocyanate, magnesium thiocyanate, calcium thiocyanate, barium thiocyanate, zinc thiocyanate, and a combination thereof.

10. The dry solid matrix of claim 1, wherein the buffer is selected from the group consisting of 2-amino-2-hydroxymethyl-propane-1,3-diol (Tris), 2-(N-morpholino)ethanesulfonic acid (MES), 3-(N-morpholino)propanesulfonic acid (MOPS), 4-(2-hydroxyethyl)-1-piperazineethanesulfonic acid (HEPES), a citrate buffer, and a phosphate buffer.

11. The dry solid matrix of claim 10, wherein the pH range is between 3 and 6.

12. The dry solid matrix of claim 3, wherein the UV protectant or free-radical trap is selected from the group consisting of hydroquinone monomethyl ether (MEHQ), hydroquinone (HQ), toluhydroquinone (THQ), and ascorbic acid.

13. The dry solid matrix of claim 4, wherein the RNase inhibitor is vanadyl ribonucleoside complex (VRC) or a commercially available RNase inhibitor.

14. The solid matrix of claim 13 further comprising a free-radical trap, wherein the free-radical trap comprises MEHQ or THQ.

15. A method for extracting and storing nucleic acids from a sample comprising:
   a) providing a dry solid matrix for extraction and storage of nucleic acids from a biological sample, where the solid matrix is a porous matrix comprising cellulose, cellulose acetate, glass fiber, or any combination thereof, and wherein a composition is incorporated into the dry solid matrix comprising,
   a metal thiocyanate comprises a Group 1 or Group 2 metal cation;
   a reducing agent ,where the reducing agent is TCEP;
   and a buffer;
   b) drying the solid matrix after incorporation of the composition into the dry solid matrix;
   c) applying a sample to the dry solid matrix to collect the nucleic acids;
   d) drying the solid matrix comprising the nucleic acids; and
   e) storing the nucleic acids on the solid matrix in a dry state under ambient conditions.

16. The method of claim 15, wherein the metal cation is selected from the group consisting of $Na^+$, $K^+$, $Li^+$, $Mg^{+2}$, $Ca^{+2}$, and $Ba^{+2}$.

17. The method of claim 15, wherein the method further comprises recovering the nucleic acids from the solid matrix.

18. The method of claim 15, wherein the biological sample is blood, serum, tissue, saliva, nasal mucous, or cells.

19. The method of claim 15, wherein the sample is a purified nucleic acid sample or a tissue culture cell preparation.

20. The method of claim 15, wherein purification of the nucleic acids from the sample is not required prior to applying the sample to the dry solid matrix for extraction and storage of the nucleic acids.

21. The method of claim 15, wherein the method permits the prolonged storage of RNA in a dry format under ambient conditions.

22. The method of claim 17, wherein the nucleic acids are recoved from the dry solid matrix by rehydrating the matrix in an aqueous solution, a buffer, or an organic solution, and wherein the nucleic acids are subjected further analysis.

23. The method of claim 17, wherein the nucleic acids are recovered from the dry solid matrix by electroelution.

* * * * *